(12) United States Patent
Vischer et al.

(10) Patent No.: US 6,872,566 B2
(45) Date of Patent: Mar. 29, 2005

(54) METHOD FOR PROCESSING A NUCLEIC ACID SAMPLE BY SWINGING A SEGMENT OF A CARTRIDGE WALL, A SYSTEM AND A CARTRIDGE FOR PERFORMING SUCH A METHOD

(76) Inventors: Peter Vischer, Seeburgstrasse 31, Küssnacht am Rigi (CH), CH-6403; Marcel Aeschilmann, Dorfgasse 65, Ligerz (CH), CH-2514

( * ) Notice: Subject to any disclaimer, the term of this patent is extended or adjusted under 35 U.S.C. 154(b) by 0 days.

(21) Appl. No.: 10/033,426

(22) Filed: Dec. 27, 2001

(65) Prior Publication Data

US 2002/0164619 A1 Nov. 7, 2002

(30) Foreign Application Priority Data

Dec. 28, 2000 (EP) ............................................. 00811252

(51) Int. Cl.[7] .............................. C12M 1/34; C12Q 1/32
(52) U.S. Cl. ........................................ 435/287.2; 435/6
(58) Field of Search ...................................... 435/287.2

(56) References Cited

U.S. PATENT DOCUMENTS

| | | | |
|---|---|---|---|
| 4,095,288 A | | 6/1978 | Garlinghouse |
| 5,658,723 A | | 8/1997 | Oberhardt |
| 5,856,174 A | | 1/1999 | Lipshutz et al. |
| 5,858,671 A | * | 1/1999 | Jones ............................. 435/6 |
| 6,309,875 B1 | * | 10/2001 | Gordon .................... 435/287.2 |

FOREIGN PATENT DOCUMENTS

| | | |
|---|---|---|
| EP | 0 695 941 A2 | 2/1996 |
| EP | 0 695 941 A3 | 12/1996 |
| EP | 0 891 811 A1 | 1/1999 |
| EP | 00 81 1252 | 5/2001 |

* cited by examiner

Primary Examiner—Jeffrey Fredman
(74) Attorney, Agent, or Firm—Townsend & Townsend & Crew LLP

(57) ABSTRACT

A method for processing a nucleic acid sample contained in a liquid comprises: (a) introducing said liquid into a chamber (41) of a cartridge (42) which contains a chip shaped carrier (44) having an active surface (45) which carries an array of oligonucleotides, said active surface (45) facing the inner surface of a wall (46) of said cartridge, said chamber (41) having a narrow interior and including a channel (43), a portion of said channel lying between said active surface (45) of said chip shaped carrier (44) and the inner surface of said wall (46), a rigid segment (47) of said wall (46) being adapted to be swung of a predetermined angle back and forth about a torsion bar (59), swinging of that segment (47) in one sense moving one end thereof towards said active surface (45), and swinging of that segment (47) in the opposite sense moving said one end of that segment (47) away from said active surface (45), (b) positioning said cartridge (42) into a cartridge holder (56) which holds said cartridge, said positioning being effected before or after introduction of said liquid containing a sample into said chamber (41), and (c) swinging said rigid segment (47) of said wall (46) of said predetermined angle back and forth about said torsion bar (59) in order to cause relative motion of the liquid contained in said channel (43) with respect to said active surface (45) of said chip shaped carrier (44).

3 Claims, 5 Drawing Sheets

Angular velocity [rad/s]

METHOD FOR PROCESSING A NUCLEIC ACID SAMPLE BY SWINGING A SEGMENT OF A CARTRIDGE WALL, A SYSTEM AND A CARTRIDGE FOR PERFORMING SUCH A METHOD

FIELD OF THE INVENTION

The present invention relates to a method for processing a nucleic acid sample contained in a liquid.

The invention further relates to a system for processing a nucleic acid sample contained in a liquid.

The invention further relates to a cartridge for processing a nucleic acid sample contained in a liquid.

The invention relates in particular to processing of a nucleic acid sample contained in a liquid introduced into a cartridge containing a chip shaped carrier having a biochemically active surface which is adapted to be read by an opto-electronic reading device.

BACKGROUND OF THE INVENTION

Within the context of the instant invention and in a preferred embodiment, a chip shaped carrier is a substrate, in particular a glass chip of e.g. squared shape having a thickness of e.g. 0.7 or 1.0 millimeter and a so called active surface, which is a surface coated with an array of different snippets of DNA or other molecular probes, e.g. DNA oligonucleotide probes, located at known positions on that surface. Those probes serve for detecting DNA fragments with a complementary DNA sequence.

Within the context of the instant invention and in a preferred embodiment the above-mentioned cartridge is in particular a cartridge made of a plastic material and used as a packaging device for packaging such a chip shaped carrier usually called DNA chip. More preferably, the cartridge is designed as a one-way cartridge.

DNA chips contained in such cartridges have a wide range of applications. For example, they may be used for understanding the structure-activity relationship between different biological materials or determining the DNA-sequence of an unknown biological material. For instance, the DNA-sequence of such unknown material may be determined by, for example, a process known as sequencing by hybridization. In one method of sequencing by hybridization, a sequences of diverse materials are formed at known locations on a surface of a chip, and a solution containing one or more targets to be sequenced is applied to that surface. The targets will bind or hybridize with only complementary sequences on the substrate. The locations at which hybridization occurs are detected with appropriate detection systems by labeling the targets with a fluorescent dye, radioactive isotope, enzyme, or other marker. Information about target sequences can be extracted from the data obtained by such detection systems.

By combining various available technologies, such as photolithography and fabrication techniques, substantial progress has been made in the fabrication and placement of diverse materials on chips of the above mentioned kind. For example, thousands of different sequences may be fabricated on a single substrate of about 1.28 square centimeter in only a small fraction of the time required by conventional methods. Such improvements make these substrates practical for use in various applications, such as biomedical research, clinical diagnostics, and other industrial markets, as well as the emerging field of genomics, which focuses on determining the relationship between genetic sequences and human physiology.

For efficient use of a chip shaped carrier of the above described type it is necessary that the sample solution containing one or more targets to be sequenced effectively contacts the active surface of the chip shaped carrier. Moreover, in view of the relatively large number of sample solutions to be processed, this effective contact should be achieved with high reproducibility and at low cost.

Known prior art attempts to attain these aims require means for pumping a liquid containing a nucleic acid sample into and out a chamber of a cartridge in order to obtain the desired effective contact between the liquid containing the sample and the active surface of the chip shaped carrier. This approach is too expensive, cumbersome and requires too much working space, and can therefore not satisfy present day requirements on this kind of apparatuses.

A main aim of the instant invention is therefore to provide a method, a cartridge and a system which make it possible to provide effective contact of a solution processed in a cartridge of the above mentioned kind with the active surface of the chip shaped carrier and this with a high reproducibility and at low cost.

SUMMARY AND MAIN ADVANTAGES OF THE INVENTION

According to a first aspect of the invention the above aim is achieved with a method for processing a nucleic acid sample contained in a liquid, said method comprising (a) introducing said sample into a chamber of a cartridge which contains a chip shaped carrier having an active surface which carries an array of oligonucleotides, said active surface facing an inner surface of a wall of said cartridge, said chamber having a narrow interior and including a channel, a portion of said channel lying between said active surface of said chip shaped carrier and the inner surface of said wall, a rigid segment of said wall being adapted to be swung about a predetermined angle back and forth about a torsion bar, swinging of said rigid segment in one sense moving one end thereof towards said active surface, and swinging of the rigid segment in an opposite sense moving said one end of the rigid segment away from said active surface, (b) positioning said cartridge into a cartridge holder which holds said cartridge, said positioning being effected before or after introduction of said sample into said chamber, and (c) swinging said rigid segment of said wall about said predetermined angle back and forth about said torsion bar in order to cause relative motion of the liquid sample contained in said channel with respect to said active surface of said chip shaped carrier. According to the first aspect of the invention the above aim is also achieved with a system for processing a nucleic acid sample contained in a liquid, said system comprising (a) a cartridge for processing a liquid nucleic acid sample, said cartridge including a chip shaped carrier having an active surface which carries an array of oligonucleotides, said active surface facing an inner surface of a wall of said cartridge, a chamber having a narrow interior and including a channel, a portion of said channel lying between said active surface of said chip shaped carrier and the inner surface of said wall, and a rigid segment of said wall being adapted to be swung about a predetermined angle back and forth about a torsion bar, swinging of the rigid segment in one sense moving one end thereof towards said active surface, and swinging of the rigid segment in an opposite sense moving said one end of the rigid segment away from said active surface; (b) a cartridge holder which is adapted to hold said cartridge in such a way that said active surface of said chip shaped carrier lies in a substantially vertical plane; and (c) means for swinging said rigid segment of said wall of said predetermined angle back and forth about said torsion bar in order to cause relative motion of the liquid contained in said channel with respect to said active surface of said chip shaped carrier. According to the first aspect of the invention the above aim is also achieved with a cartridge for processing a nucleic acid sample contained in a liquid, said cartridge comprising (a) a chip shaped carrier having an active surface which carries an array of oligonucleotides, said active surface facing an inner surface of a wall of said cartridge, (b) a chamber having a narrow interior and including a channel, a portion of said channel lying between said active surface of said chip shaped carrier and the inner surface of said wall, and (c) a rigid segment of said wall being adapted to be swung about a predetermined angle back and forth about a torsion bar, swinging of said rigid segment in one sense moving one end thereof towards said active surface, and swinging of said rigid segment in the opposite sense moving said one end of said rigid segment away from said active surface. Features of preferred embodiments are described herein.

The main advantages of the invention are that it makes possible to achieve the above mentioned, desirable effective contact between the sample solution and the active surface of the chip shaped carrier with high reproducibility and with simple means which in turn makes possible to achieve all this at low cost. This latter advantage becomes very important when a plurality of cartridges each containing a liquid containing a sample have to be simultaneously processed.

SHORT DESCRIPTION OF THE DRAWINGS

A preferred embodiment of the invention is described hereinafter more in detail with reference to the accompanying drawings, wherein FIG. 1 shows a schematic cross-sectional representation of a cartridge 42 according to the invention including the drive unit.

FIG. 2 shows an perspective exploded view of components of cartridge 42 showing in particular the interior of chamber 41 and channel 43 formed in a chip plate 52 which is part of cartridge 42.

FIG. 3 shows an perspective exploded view of components of cartridge 42 seen from a point of view opposite to the one of FIG. 2.

FIG. 4 shows a top view of the channel plate 51 of cartridge 42 and of channel 43 thereof.

DETAILED DESCRIPTION OF A PREFERRED EMBODIMENT

Figure 1:
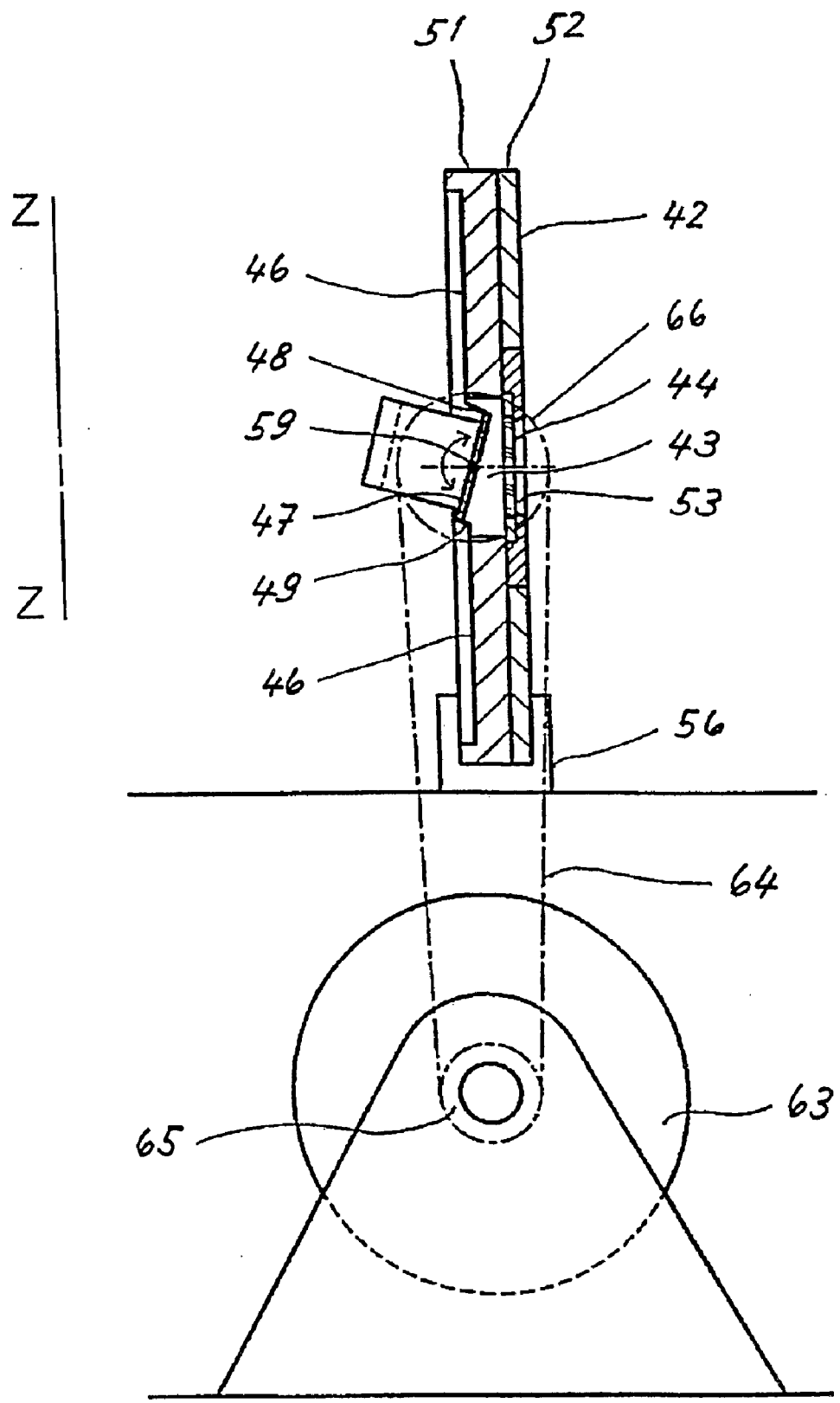

As schematically represented in FIG. 1, a cartridge 42 according to the invention comprises a chamber 41 and chip shaped carrier 44.

Chip shaped carrier 44 has an active surface 45 which carries an array of oligonucleotides and which faces the inner surface of a wall 46 of cartridge 42.

Chamber 41 of cartridge 42 has a narrow interior and includes a channel 43. A portion of channel 43 lies between active surface 45 of chip shaped carrier 44 and the inner surface of wall 46.

As depicted in FIG. 1 cartridge 42 comprises a channel plate 51 which comprises and essentially defines the shape of chamber 41 and channel 43, and a chip plate 52 which is adapted to receive and hold chip shaped carrier 44 at the position shown in FIG. 1 within a cavity 53 of chip plate 52.

When channel plate 51 and chip plate 52 are assembled together to form cartridge 42, this cartridge has an inlet which allows to introduce a predetermined volume of a liquid containing a nucleic acid sample into chamber 41 of cartridge 42 by means of a pipetting needle which is part of an automatic pipetting unit. Cartridge 42 also has an outlet which allows to remove said liquid sample from cartridge 42 if and when desired.

Chamber 41 and channel 43 are cavities comprised between an inner surface of channel plate 51 and an inner surface of chip plate 52. These inner surfaces are substantially opposite to each other.

Channel plate 51, chip plate 52 and other parts of cartridge 42 are made preferably of plastic materials which are suitable manufacture by injection molding and also for carrying out the envisaged process steps for processing a liquid sample of the above mentioned kind. Such plastic materials should be chemically inert so that they cannot interfere with the processing of the samples. Moreover the material chosen for the manufacture of components of cartridge 42 should not be fluorescent, so that they cannot interfere with fluorescence measurements usually performed after processing the liquid samples. Channel plate 51 and chip plate 52 can but must not necessarily be transparent.

The upper part of channel plate 51 comprises projections or tongues (not shown) which are integral parts of cartridge 42 and which are so configured and dimensioned that they are adapted to be grasped by a suitable gripper of a transport device in order to transport and insert a cartridge 42 into a cartridge holder 56 and to remove a cartridge 42 from that cartridge holder.

The process of manufacture of cartridge 42 comprises positioning and fixing chip shaped carrier 44 into a corresponding cavity 53 available in chip plate 52 by suitable means, and assembling together channel plate 51 and chip plate with carrier 44 attached to it in order to form a cartridge 42 ready for use, wherein the active surface 45 of carrier is at the above mentioned position with respect to channel 43. The just mentioned assembling of channel plate 51 and chip plate 52 forms chamber 41 and channel 43 within cartridge 42.

The means for positioning and fixing chip shaped carrier 44 into cavity 53 available in chip plate 52 are preferably those described in co-pending European patent application No. 00810501.7 entitled "Device for packaging a chip shaped carrier and process for assembling a plurality of such carriers" filed on Jun. 8, 2000 by the applicant of this application.

Cartridge 42 has a structure which has in particular the following features:

A rigid segment 47 of wall 46 is adapted to be swung of a predetermined angle back and forth about a torsion bar 59 and with respect to an initial position at which wall segment 47 is coplanar with wall 46. In order to enable the latter swinging motion of rigid wall segment 47, this segment is connected by elastic wall segments 48 and 49 to the remaining part of wall 46.

When wall segment 47 is swung in a first sense, one end of wall segment 47 is moved towards active surface 45, and when wall segment 47 is swung in a second sense opposite to the first sense, the latter end of wall segment 47 is moved away from active surface 45. The preferred size of the predetermined swinging angle lies between six and twelve degrees. This predetermined swinging angle is measured with reference to the position of wall segment 47 at which this segment is coplanar with wall 46.

In order to perform a method according to the invention cartridge 42 is inserted and thereby positioned into a cartridge holder 56 which is represented schematically in FIG. 1.

Cartridge 42 and cartridge holder 56 are so configured that when cartridge 42 is positioned into cartridge holder 56 the active surface 45 of chip shaped carrier 44 lies in a substantially vertical plane, though the active surface 45 does not need to be vertical, it may also be inclined or even horizontal, even if these variants are expected to perform less.

In FIG. 1 the position of a vertical plane is represented by a straight line Z—Z.

Figure 5:
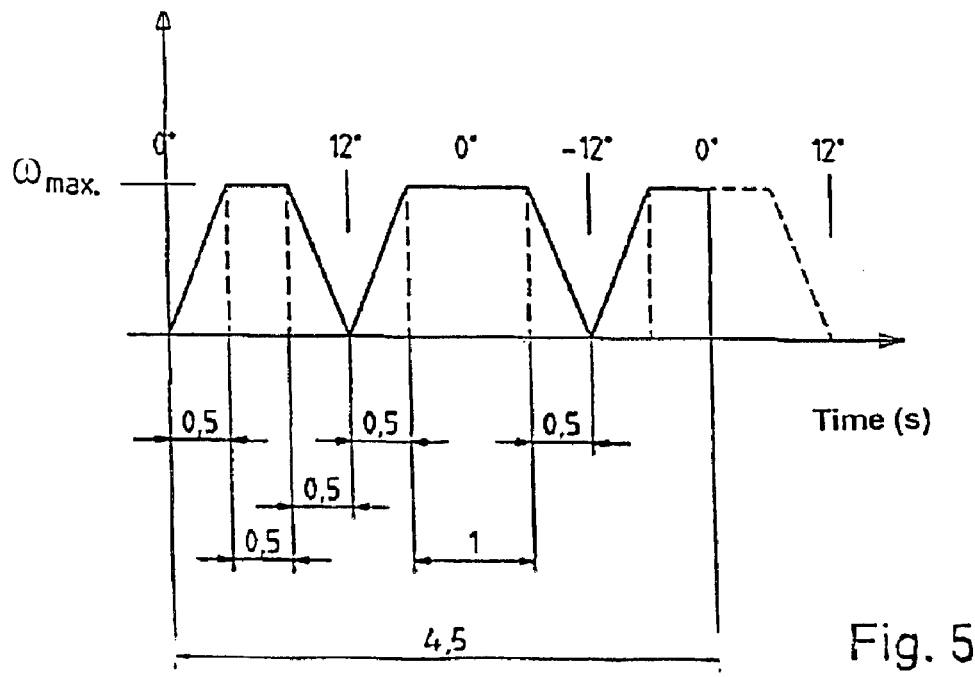
FIG. 5 shows a diagram of the variation of the angular velocitiy $\omega = d\theta/dt$ with time for the swinging movement of rigid wall segment 47.

FIG. 5 shows as an example a diagram of the variation of the angular velocity $\omega = d\theta/dt$ with time which is achievable with the above described means for oscillating rigid wall segment 47 for the case where the angle of oscillation varies between plus 12 degrees and minus 12 degrees. With the values shown in this diagram the oscillation frequency is 0.25 cycle per second and the maximal angular velocity is about 0.2 rad per second or 11.5 degrees per second. An oscillation according to the diagram of FIG. 5 is used for instance during the sample hybridization step described hereinafter. For the sample rinse step described hereinafter the variation of the angular velocity of oscillation with time has a similar shape as in FIG. 5, but the oscillation frequency is e.g. of 0.4 cycle per second.

In a preferred embodiment, the function angular velocity vs. time differs from the one shown by FIG. 5 and has approximately a sinusoidal shape in order that the movement parameters (location, velocity, acceleration) vary substantially smoothly.

A system according to a second aspect of the invention comprises a cartridge 42 and a cartridge holder 56 having the above described features and comprises in addition means for swinging the above mentioned segment of wall 46 of a predetermined angle back and forth around a torsion bar 59 in order to cause relative motion of the liquid sample contained in channel 43 with respect to active surface 45 of chip shaped carrier 44. The means for swinging wall segment 47 comprise e.g. a step motor 63 and suitable drive means (belt 64 and pulleys 65 and 66) connecting this motor 63 to wall segment 47.

Figure 2:
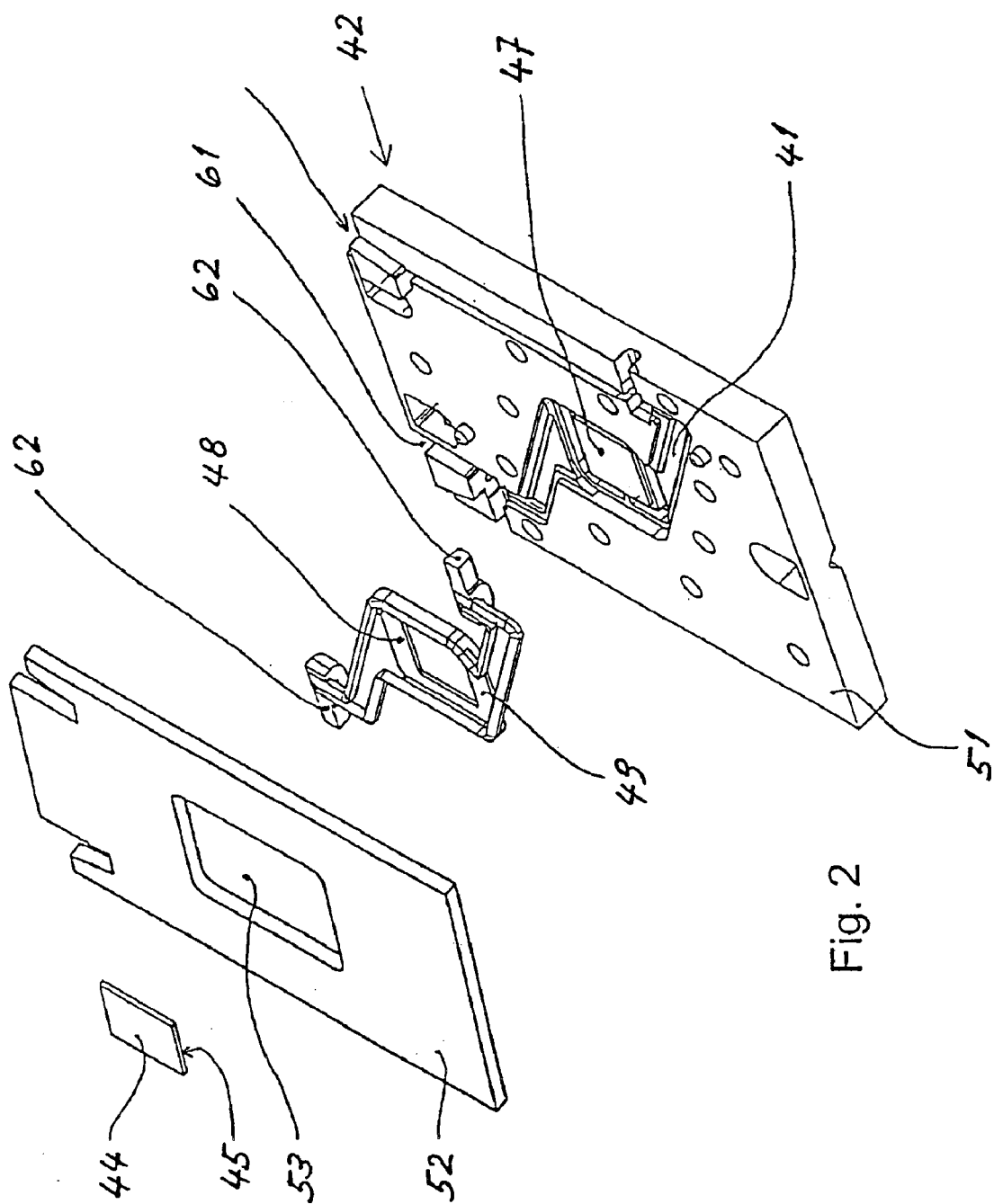

FIG. 2 shows in particular channel 43, rigid segment 47 of wall 46, torsion bar 59.

Channel plate 51 is a two-component part made by injection molding which is composed of a hard channel plate and a soft thermoplastic material, e.g. an elastomer which has several functions as part of cartridge 42. Plugs 62 and 63 seal and thereby separate channel 43 from its environment. Plug 62 is pierced by a first hollow needle for introducing or removing a liquid into channel 43. During such steps plug 63 is also pierced by a second hollow needle for venting channel 43. Plugs 62 and 63 effectively seal channel 43 even after being pierced several times by the hollow needles.

Elastic segments 48 and 49 of wall 46 are the portions of the elastomer material which undergo the largest deformation during use of the cartridge.

Chip plate 52 is also made by injection molding, and is preferably as well a two-component part. Cavity 53 of chip plate 52 is filled by chip shaped carrier 44 (not shown).

Figure 3:
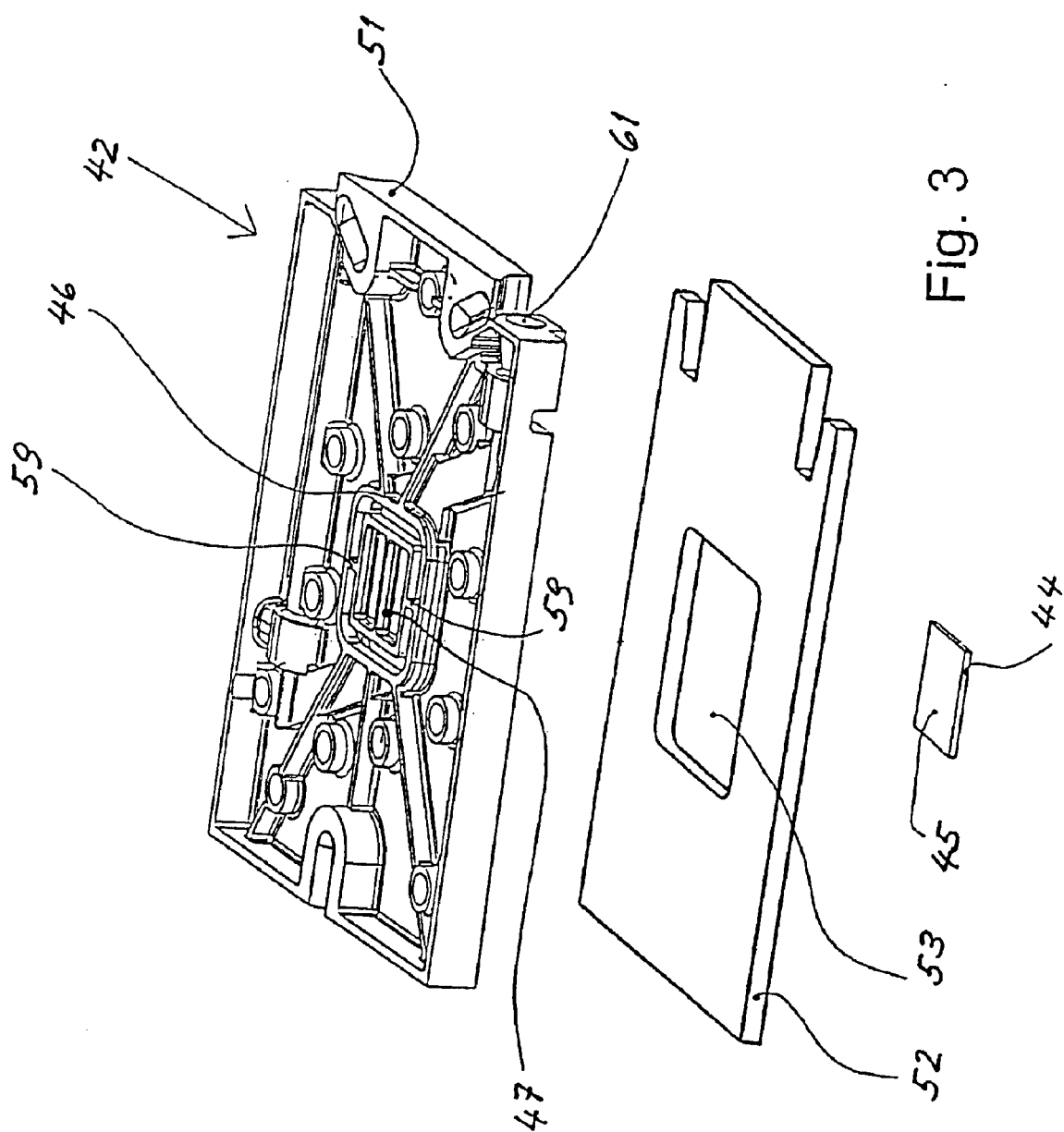

FIG. 3 shows an perspective exploded view of components of cartridge 42 seen from a point of view opposite to the one of FIG. 2. FIG. 3 shows in particular torsion bar 59 about which rigid segment 47 of wall 46 is swung back and forth e.g. of an angle of plus/minus 12 degrees. The soft plastic component of channel plate 51 is not shown by FIG. 3.

Figure 4:
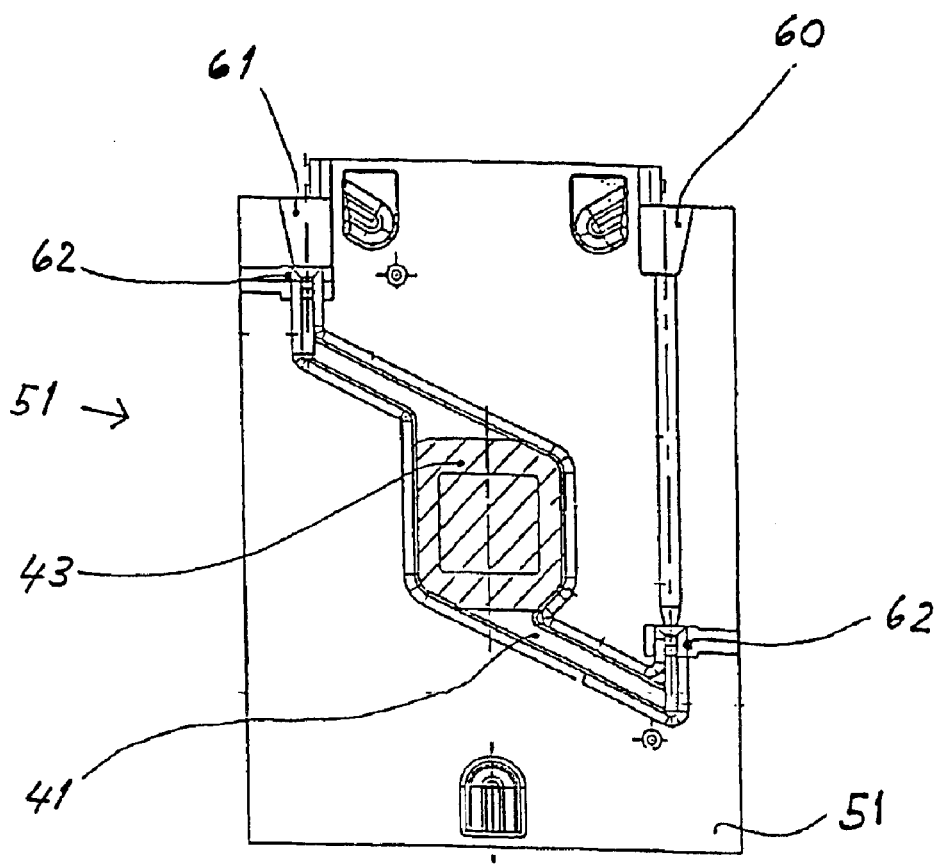

The top view shown by FIG. 4 shows particularly well plugs 62 and 63.

A method for processing a nucleic acid sample contained in a liquid according to a second aspect of the invention can be carried out with the means described in this Example 2 and comprises the following steps:

(a) introducing a liquid containing a nucleic acid sample into chamber 41 of cartridge 42 and thereby into channel 43 of chamber 41, (b) positioning cartridge 42 into cartridge holder 56 in such a way that active surface 45 of chip shaped carrier 44 lies in a substantially vertical plane, this positioning of cartridge 42 into cartridge holder 56 being effected before or after introduction of the liquid containing a sample into chamber 41, and (c) swinging the above mentioned segment 47 of wall 46 of a predetermined angle back and forth around a torsion bar in order to cause relative motion of the liquid containing a sample contained in channel 43 with respect to active surface 45 of chip shaped carrier 44.

The latter swinging of wall segment causes a forced flow of fluid within channel 43 and generates a flow which provides a mixing effect which is advisable for the hybridizing step described hereinafter. Moreover the shape of chamber 41 and channel 43 are such that the entire active surface 45 is uniformly contacted by the liquid containing a sample.

Figure 6:
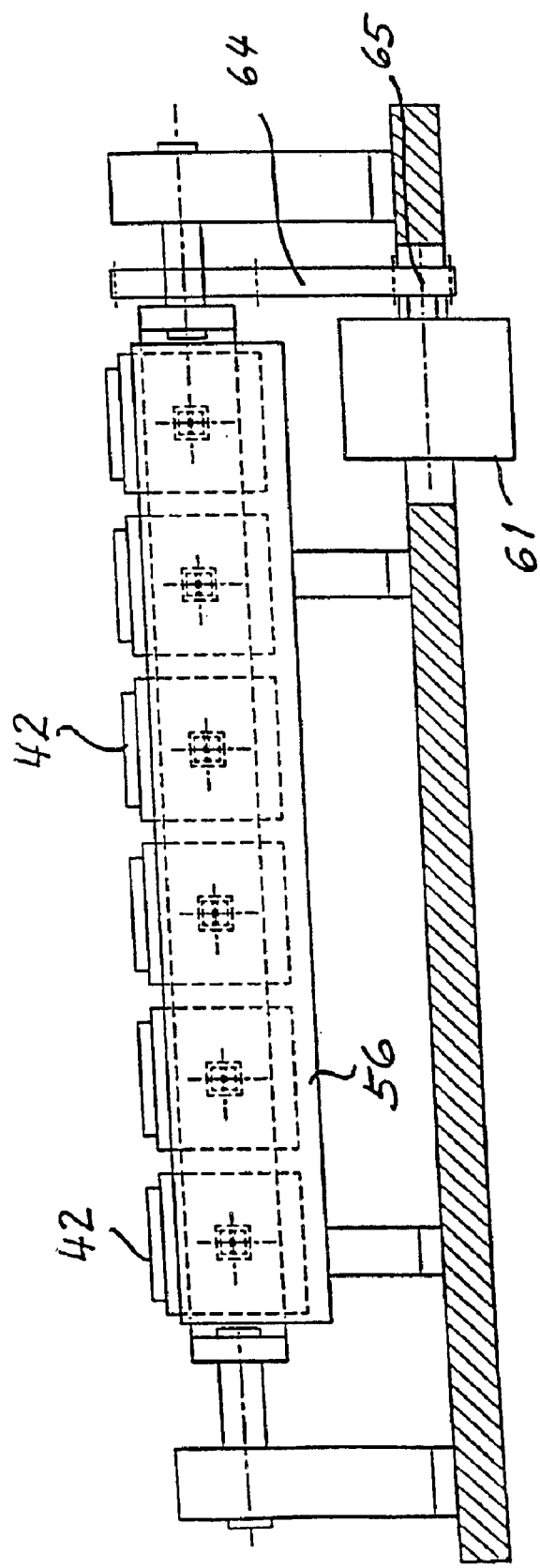
FIG. 6 shows a system according to the invention for simultaneously handling a plurality of cartridges 42.

According to a preferred embodiment of the invention a method of the type just described is carried out simultaneously on a plurality of cartridges by means of a system according to the invention adapted for that purpose as shown by FIG. 6.

A typical use of a method, cartridge and system according to the invention is for carrying out process steps of a so called post PCR processing of a liquid containing a nucleic acid sample which has been amplified by means of a PCR method or the like.

Such post PCR processing carried out using cartridge 42 includes in general terms the following steps: introducing liquid into chamber 41 and into channel 43 of cartridge 42 at some points of time and withdrawing liquid from chamber 41 and channel 43 of cartridge 42 at other points of time, repeating this steps several times, and heating and cooling cartridge 42 during predetermined time intervals according to predetermined temperature profiles, e.g. in a temperature range between zero and seventy degrees Celsius. The liquid containing the nucleic acid sample being one of the liquids introduced into and withdrawn from cartridge or 42, another type of liquid handled in this way as part of the method being e.g. buffer liquid used for rinsing chamber 41 and channel 43 during rinsing steps mentioned hereinafter.

More in detail a post PCR processing of an amplified nucleic acid sample using the devices described above comprises e.g. the following steps:

1) Introduction of the Liquid Containing an Amplified Nucleic Acid Sample into the Cartridge This liquid is introduced into cartridge 42 through an inlet thereof and by means of the pipetting needle of an automatic pipetting unit.

2) Sample Hybridization

During an hybridization step by means of heat transfer the temperature of the cartridge is maintained at a predetermined level. Over the whole duration of this step, which takes between 30 and 60 minutes, a relative movement of the liquid containing a sample with respect to the active surface of the chip shaped carrier and thereby a flow of that liquid over that surface is effected by the means described above. In connection with this step it is important to note that the chamber and the channel within the cartridge are so configured that a uniform distribution of the liquid over the active surface of the chip shaped carrier is achieved.

3) Sample Rinse

In a first washing step (rinse) the interior of cartridge 42 is rinsed with a washing buffer which flows into the cartridge thorough an inlet thereof and leaves it through an outlet thereof. This step is repeated up to ten times.

4) Rinse Incubation

This step serves for stabilizing the processing of the liquid containing a sample contained in the cartridge. During this step which takes about 15 minutes, the liquid sample is kept at a lower temperature level than during the hybridization step and is moved with respect to the active surface of the chip shaped carrier in the same way as during the hybridization step.

5) Stain Hybridization

In this step a fluorescent solution is added to the liquid containing a sample contained in the cartridge in order that individual fluorescing molecules can get attached to DNA fragments. During this step the cartridge is kept again at a higher temperature level.

6) Stain Rinse

In this step remaining free fluorescing molecules are washed out of the cartridge by means injecting a washing buffer through an inlet of the cartridge at a suitable first position thereof and changing the position cartridge to a second position at which liquid carrying those free fluorescing molecules is withdrawn from the cartridge through an outlet thereof. This step is repeated up to ten times.

7) Detection

After step 6) the sample is bound to the active surface 45 of chip shaped carrier 44, this surface is flooded with a sample-free buffer, and the cartridge containing the liquid containing a sample is transferred by suitable transport means which include a gripper to a detection unit, where the surface of the active surface of chip shaped carrier is scanned with a laser beam and fluorescent light emerging from said active surface in response to that excitation is measured by means of suitable instrument. In order that this detection can be performed the cartridge has an opening through which the chip shaped carrier and the active surface thereof are accessible to opto-electronic examination.

| List of reference numbers | |
|---|---|
| 41 | chamber |
| 42 | cartridge |
| 43 | channel |
| 44 | chip shaped carrier of an array of oligonucleotides |
| 45 | active surface of carrier 44 |
| 46 | wall of channel plate 51 |
| 47 | rigid segment of wall 46 |
| 48 | elastic segment of wall 46 |
| 49 | elastic segment of wall 46 |
| 51 | channel plate |
| 52 | chip plate |
| 53 | cavity of chip plate |
| 56 | cartridge holder |
| 59 | torsion bar |
| 60 | inlet/outlet |

-continued

| List of reference numbers | |
|---|---|
| 61 | air exchange opening |
| 62 | plug |
| 63 | step motor |
| 64 | belt |
| 65 | pulley |
| 66 | pulley |
| Z–Z | a vertical straight line |

Modifications and alternative embodiments of the invention will be apparent to those skilled in the art in view of the foregoing description. Accordingly, this description is to be construed as illustrative only and is for the purpose of teaching those skilled in the art the best mode of carrying out the invention. Details of the apparatus and of the method described may be varied without departing from the spirit of the invention and the exclusive use of all modifications which come within the scope of the appended claims is reserved.

What is claimed is:

1. A system for processing a nucleic acid sample contained in a liquid, said system comprising
   (a) a cartridge for processing a liquid nucleic acid sample, said cartridge including
   (a.1) a chip shaped carrier having an active surface which carries an array of oligonucleotides, said active surface facing an inner surface of a wall of said cartridge,
   (a.2) a chamber having a narrow interior and including a channel, a portion of said channel lying between said active surface of said chip shaped carrier and the inner surface of said wall, and
   (a.3) a torsion bar attached to a rigid segment of said wall said rigid segment being adapted to be swung about a predetermined angle back and forth with respect to the active surface about the torsion bar, swinging of the rigid segment in one sense moving one end thereof towards said active surface, and swinging of the rigid segment in an opposite sense moving said one end of that segment away from said active surface,
   (b) a cartridge holder which is adapted to hold said cartridge in such away that said active surface of said chip shaped carrier lies in a substantially vertical plane, and
   (c) means for swinging said rigid segment of said wall of said predetermined angle back and forth about said torsion bar in order to cause relative motion of the liquid sample contained in said channel with respect to said active surface of said chip shaped carrier.

2. A system according to claim 1, wherein the cartridge is held by the cartridge holder in such a way that said active surface of said chip shaped carrier lies in a substantially vertical plane.

3. A cartridge for processing a nucleic acid sample contained in a liquid, said cartridge comprising
   (a) a chip shaped carrier having an active surface which carries an array of oligonucleotides, said active surface facing the inner surface of a wall of said cartridge,
   (b) a chamber having a narrow interior and including a channel, a portion of said channel lying between said active surface of said chip shaped carrier and the inner surface of said wall, and
   (c) a torsion bar attached to a rigid segment of said wall said rigid segment being adapted to be swung of a predetermined angle back and forth about the torsion bar, swinging about said rigid segment in one sense moving one end thereof towards said active surface, and swinging of said rigid segment in the opposite sense moving said one end of said rigid segment away from said active surface.

* * * * *

UNITED STATES PATENT AND TRADEMARK OFFICE
CERTIFICATE OF CORRECTION

PATENT NO. : 6,872,566 B2
DATED : March 29, 2005
INVENTOR(S) : Peter Vischer and Marcel Aeschlimann It is certified that error appears in the above-identified patent and that said Letters Patent is hereby corrected as shown below:

<u>Title page,</u>
Item [76], Inventor, delete "Marcel Aeschilmann" and replace with -- Marcel Aeschlimann. --
Item [73], insert -- Assignee, Roche Molecular Systems, Inc Alameda, California (US) --

Signed and Sealed this

Twelfth Day of July, 2005

JON W. DUDAS
*Director of the United States Patent and Trademark Office*